United States Patent [19]

Lynch et al.

[11] Patent Number: 4,695,410
[45] Date of Patent: Sep. 22, 1987

[54] RECOVERY OF PHENOL FROM AQUEOUS SOLUTION

[75] Inventors: Gary J. Lynch, Bridgeton; Chen-Hsyong Yang, Chesterfield, both of Mo.

[73] Assignee: Monsanto Company, St. Louis, Mo.

[21] Appl. No.: 901,681

[22] Filed: Aug. 29, 1986

[51] Int. Cl.$^4$ .......................... C07F 5/8; C07C 37/68; C07C 69/7

[52] U.S. Cl. .................. 260/410.5; 568/749; 568/748

[58] Field of Search .............. 568/748, 749; 260/410.5

[56] References Cited

U.S. PATENT DOCUMENTS 2,807,654 9/1955 Grimmett et al. .............. 260/627
3,772,389 6/1971 Lowrance .......................... 268/465
4,271,311 7/1979 Knickmeyer ...................... 560/86
4,325,789 4/1982 Wust et al. ........................ 568/749

FOREIGN PATENT DOCUMENTS 0207543 3/1984 Fed. Rep. of Germany ...... 568/749

Primary Examiner—Werren B. Lone
Attorney, Agent, or Firm—R. Loyer; A. Hoffman; A. Cole

[57] ABSTRACT

The disclosed process is employed to recover phenol from aqueous solutions produced by distillation of the product of a process for producing a phenyl ester by the reaction of a carboxylic acid and phenol. Purified phenyl ester is employed to extract phenol from the aqueous solution. The extract is combined with raw product for recovery of the phenol and phenyl ester. In a preferred embodiment the process for producing the phenyl ester is continuous and the extract containing phenol and phenyl ester are fed to the dewatered ester stream for product recovery.

10 Claims, 1 Drawing Figure

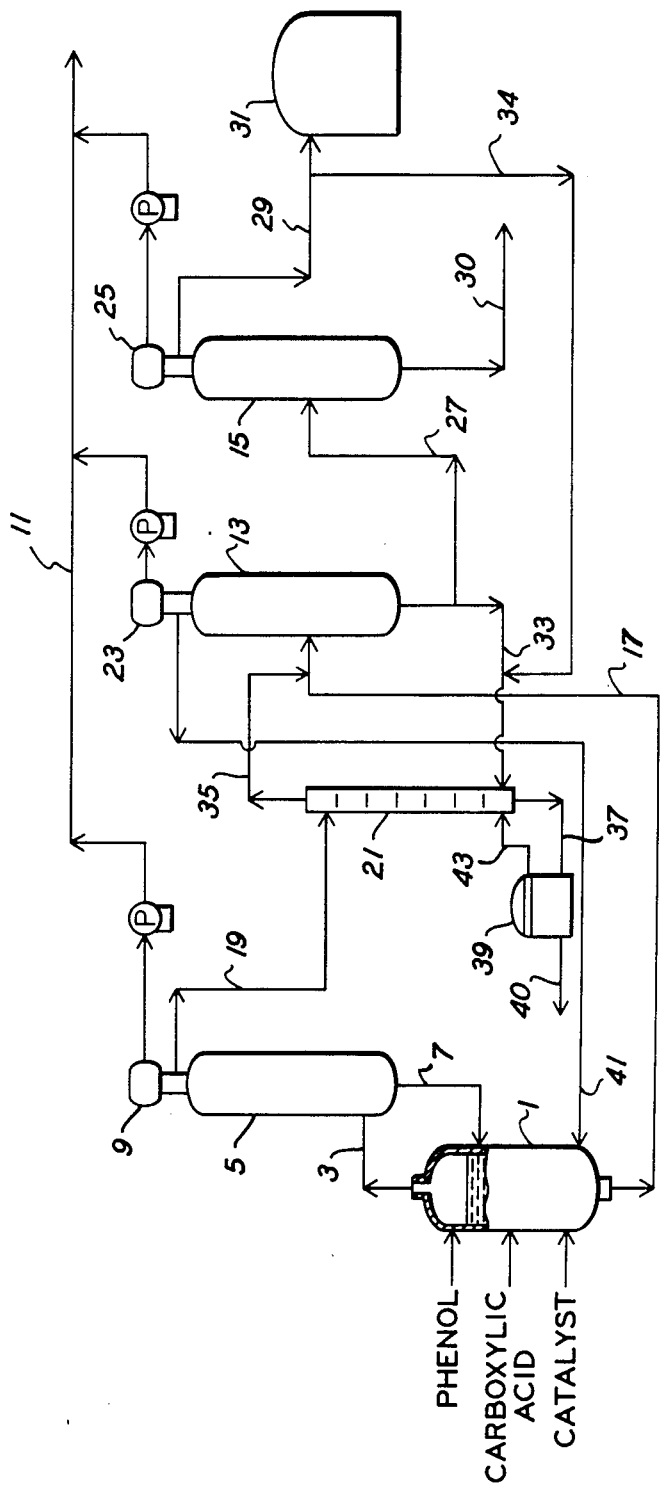

RECOVERY OF PHENOL FROM AQUEOUS SOLUTION

This invention relates to the recovery of phenol from aqueous solutions. The invention relates more particularly to a process enabling the efficient removal of phenol from aqueous solutions and recovery of both the extractant and phenol in an economically efficient manner.

It is well known to produce phenyl esters by esterification of phenol with carboxylic acids. Typical processes are described in U.S. Pat. Nos. 3,772,389 to Lawrence, Jr. issued Nov. 13, 1973, and 4,271,311 to Knickmeyer et al, issued June 2, 1981. Another typical example of preparing phenyl esters by the reaction of a carboxylic acid with phenol is disclosed in U.S. Pat. No. 4,478,754 to Kong-Chan, issued Oct. 23, 1984. Most such reactions are catalyzed by various means as disclosed in said patents. Also, it is disclosed that water is formed during the reaction and should be removed as the reaction proceeds. Normally, the reaction temperature is sufficiently high such that the water is distilled as an azeotrope of water and phenol. There is thus presented the problem of recovering the phenol from a large quantity of water since discharge of the water without the removal of phenol is economically and ecologically unacceptable.

Attempts in the past to provide efficient removal of phenol from aqueous solution have involved the use of extraneous solvents which extract the phenol from the aqueous solution. Such systems require the recovery of the solvent. An efficient means for large volume operations in themselves create an ecological problem with respect to inadvertent losses during recovery of the solvent and phenol.

A typical example of the solvent extraction process is disclosed in U.S. Pat. No. 2,807,654 to Grimmett et al, issued Sept. 24, 1957. This patent discloses the utility of diisopropyl ether as a preferred organic solvent for carrying out liquid phase extraction of phenol from aqueous solution. Other oxygen-containing organic solvents are suggested.

In large scale processes there is a need to efficiently remove phenol from water produced during the reaction of a carboxylic acid with phenol. Eliminating the phenol from the water enables one to simply discharge the water in an ecologically acceptable manner. Extraction of phenol from aqueous solution without introducing additional materials in the process would be advantageous.

SUMMARY OF THE INVENTION

In accordance with the present invention there is provided an improved process for producing a phenyl ester by direct reaction of a carboxylic acid with phenol. As is customary in such reactions the water produced during the reaction is removed to provide a more efficient reaction. The water removed contains considerable amounts of phenol which in accordance with this invention is extracted with phenyl ester produced in the same process, thereby obviating the need for extraneous solvents being introduced into the system. The phenyl ester employed in the novel extraction process of this invention may be either crude phenol stripped or further distilled or purified product which is recycled to a means for extracting phenol from aqueous solution. The phenyl ester and phenol extracted from the water are inserted into the purification system required for recovery of the product produced in the initial reaction of phenol and carboxylic acid. There is thus provided herein an extraction process which does not require extra recovery steps for both the phenol and phenyl ester contained in the extract.

DETAILED DESCRIPTION OF THE INVENTION

Phenyl esters are produced in accordance with the prior art by a direct reaction of phenol with a carboxylic acid according to the following equation:

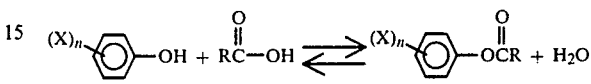

In the above equation X is a non-interfering substituent and n is an integer from 0 to 5 provided that at least one of the substituents X of the formula must be a hydrogen atom when positioned adjacent the hydroxyl group. The remaining substituents X can be the same or different monovalent substituents bound to the ring by covalent bonds and can be any such substituent which does not hinder or otherwise prevent the hydroxyl group of the phenolic compound from entering into the reaction with the carboxylic acid compound.

The above reaction is equilibrium limited and can only be driven to a reasonable degree of completeness by continuously removing the water as formed or as is available from the equilibrium limitation. The distillate actually removed is a water/phenol mixture due to azeotrope formation.

As can be seen from the prior art, the above reaction is normally catalyzed by an acid catalyst.

Also, in the above-described reaction, R is a hydrocarbyl radical which provides a carboxylic acid having a boiling point above that of the phenol/water azeotrope. The hydrocarbyl group can be any non-interfering group in the esterification reaction and may be straight or branched chain, aliphatic or aromatic and can be substituted with radicals such as alkoxy groups, halogen, sulfo or nitro groups. Aliphatic R groups include methylpropyl n-butyl, isobutyl, n-pentyl, hexyl, octyl, nonyl, decyl, undecyl, etc.

The phenyl ester must be liquid at convenient temperatures and pressure to facilitate its use as a solvent for phenol extraction. As is well known in the art, the size of the extraction column is related to the distribution coefficient of phenol in water and phenyl ester. Extraction columns of convenient size are employed when the distribution coefficient is greater than 1.

BRIEF DESCRIPTION OF THE DRAWINGS

The attached FIGURE is a flow diagram of a typical process whereby a phenyl ester is produced by the reaction of a carboxylic acid with phenol whereby water is removed continuously and the phenyl ester refined by multiple distillation. In accordance with this invention a portion of purified phenyl ester obtained from the reaction is employed in countercurrent extraction of the phenol from aqueous solution.

DETAILED DESCRIPTION OF THE DRAWINGS

In the attached drawing, phenol, a carboxylic acid and, in most cases a suitable catalyst, are combined in a reactor equipped with means to control the reaction temperature and to remove water formed during the reaction. The reaction temperature is maintained typically in the range of from about 180° C. to about 235° C. for a typical carboxylic acid such as nononoic acid. It has been noted that higher temperatures result in an undesired by-product formation. When acidic catalysts are employed there is a side reaction leading to by-product ortho and para acyl phenols. Temperatures are preferably maintained in the range of from about 190° C. to about 210° C.

During the reaction the water is continuously removed through line 3 to a dewatering column 5. A small amount of reflux is permitted to return to reactor 1 through line 7. Water is condensed in total condenser 9 and vacuum system 11 provides vacuum to all of the columns in the system including distillation columns 13 and 15. An aqueous phenol solution is taken from dewatering column 5 through line 19 to an extraction column 21.

The raw reaction product, usually containing approximately 50% phenyl ester, together with unreacted phenol and carboxylic acid, water and by-products is fed through line 17 from reactor 1 to series distillation columns 13 and 15. Each column is equipped with total condensers 23 and 25 connected to the distillation columns by feed and return lines. Phenol stripped phenyl ester is fed from column 13 to column 15 through line 27 and final purified phenyl ester product is removed from distillation column 15 through line 29 to product storage 31. Typical distillation temperatures for the exemplary nonanoyl phenyl ester are in the range of from about 215° to about 230° C. The residue from column 15 is discharged to waste through line 30 and properly destroyed.

To perform the novel phenol extraction process of this invention a portion of the crude phenol stripped phenyl ester from column 13 is withdrawn and fed through line 33 to extraction column 21. Optionally, distilled phenyl ester may be employed in the novel phenol extraction process of this invention by withdrawing an appropriate amount of the distilled ester from column 15 through line 34.

In extraction column 21 a countercurrent flow pattern is achieved by feeding distilled phenyl ester in at the bottom and the aqueous phenol solution in at the top. As phenyl ester passes through the aqueous solution phenol and phenyl ester form an organic phase which is removed through line 35 from the top of the column. Extraction column 21 is operated at a temperature which conveniently maintains the contents in the liquid state. The column size, as noted above, is dependent upon the distribution coefficient of phenol in water and phenyl ester. In the case of the exemplary nonanoic acid the distribution coefficient is 10 at about 55° C. and a five theoretical stage column has been found to be satisfactory.

The extracted phenol together with the phenyl ester is recovered by delivery through line 35 to line 17 and then through distillation columns 13 and 15. The phenol is removed from the phenyl ester in column 13 and returned through line 41 to reactor 1 together with other recovered starting materials from distillation column 13.

Water from the bottom of extraction column 21 is relatively free of phenol and can contain as low as about 40 parts per million phenol. The extracted water is preferably fed to a surge tank 39 for temporary holding before discharge to waste through line 40. A small amount of scum is accumulated in tank 39 which is returned to extraction column 21 through line 43.

There is described above a method whereby phenol is extracted from aqueous solution obtained from the reaction of a carboxylic acid and phenol. In a preferred embodiment, the process described above is continuous; however, batch operation is also feasible.

EXAMPLE

There is shown below a flow diagram illustrative of a five stage countercurrent flow column. In the diagram E represents the extract which leaves after stage 1 at the bottom of the column. Also shown in the diagram is feed solution (F) containing water and phenol while S represents purified phenyl ester (in this example phenyl-nonanoate), also referred to in the table below as "ESTER". R in the diagram below represents the raffinate comprising mostly water with a small amount of fatty acid (FA), phenyl ester and phenol. The analytical results reported for the raffinate in each stage was obtained by liquid chromatography. Below the five stage diagram there is also shown analytical results of samples of extract E drawn from each stage of the column said results having been obtained by gaseous chromatography. Because these calculations were not normalized, results in excess of 100 percent for phenyl ester are shown. Analytical results indicate that phenol in the raffinate was reduced from 30 weight percent to only 37 ppm in the five stage extraction column.

| COLUMN THEORETICAL STAGES | | | | | | |
|---|---|---|---|---|---|---|
| F | $R_1$ | $R_2$ | $R_3$ | $R_4$ | $R_5$ | |
| → | → | → | → | → | → | |
| ← | ← | ← | ← | ← | ← | |
| $E_1$ | $E_2$ | $E_3$ | $E_4$ | $E_5$ | S | |

| STEADY STATE STREAM COMPOSITION | | | | | | | | | | | |
|---|---|---|---|---|---|---|---|---|---|---|---|
| Stream | F | $E_1$ | $R_1$ | $E_2$ | $R_2$ | $E_3$ | $R_3$ | $E_4$ | $R_4$ | $E_5$ | $R_5$ | S |
| Water % | 70 | 2.70 | — | 0.50 | — | 0.29 | — | 0.26 | — | 0.25 | — | 0.00 |
| Phenol % | 30 | 29.49 | 5.03 | 3.84 | 0.51 | 0.54 | (735) | 0.09 | (126) | 0.03 | (37) | 0.00 |
| FA % | 0 | 0.70 | — | 1.01 | — | 1.02 | — | 0.86 | — | 0.78 | — | 0.25 |
| ESTER % | 0 | 66.27 | — | 96.26 | — | 99.52 | — | 102.53 | — | 101.23 | — | 99.72 |

Phenol concentration is ppm in ( )

The process of this invention is applied with particular advantage since a wide range of concentrations of aqueous phenol can be efficiently treated. Waste is avoided by utilizing crude phenol stripped or distilled phenyl ester and returning the phenyl ester together with extracted phenol to the product recovery system. No foreign substances are introduced and the extracted phenol is conveniently recycled to the reactor for further use.

Although the invention is described with respect to specific embodiments, the details thereof are not to be construed as limitations except to the extent indicated in following the claims.

What is claimed is:

1. In a process for producing a phenyl ester wherein a carboxylic acid is reacted with phenol and water is removed from the reaction product resulting in the formation of an aqueous solution of phenol, the improvement which comprises extracting phenol from the aqueous solution with recycled phenol stripped phenyl ester.

2. A process of claim 1 wherein the extract is combined with raw reaction product whereby phenol and phenyl ester are recovered.

3. The process of claim 1 wherein the carboxylic acid contains from 5 to 12 carbon atoms.

4. The process of claim 3 wherein the carboxylic acid is nonanoic acid.

5. The process of claim 1 wherein the extraction is performed in a countercurrent extraction column.

6. The process of claim 1 wherein the recycled phenyl ester is also purified by distillation prior to extraction of phenol from aqueous solution.

7. The process of claim 1 wherein the process is continuous.

8. The process of claim 1 wherein the process is carried out batchwise.

9. The process of claim 4 wherein the aqueous solution of phenol is maintained in the range of from about 50° C. to about 100° C. during extraction.

10. The process of claim 5 wherein the column has five theoretical stages.

* * * * *